United States Patent [19]

Mans et al.

[11] Patent Number: 5,776,701
[45] Date of Patent: Jul. 7, 1998

[54] MATERIALS AND METHODS FOR DETECTING OXALATE

[75] Inventors: Rusty Jay Mans; Christopher D. Batich, both of Gainesville, Fla.; Ian McFetridge, Brookline, Mass.

[73] Assignee: University of Florida, Gainesville, Fla.

[21] Appl. No.: 656,798

[22] Filed: May 31, 1996

[51] Int. Cl.$^6$ .................. G01N 33/573; C12Q 1/28; C12Q 1/26; C12Q 1/00
[52] U.S. Cl. ................ 435/7.4; 435/28; 435/25; 435/4; 435/814; 435/287.1; 422/50
[58] Field of Search .............. 435/7.4, 28, 25, 435/4, 814, 287, 287.1; 422/50

[56] References Cited

U.S. PATENT DOCUMENTS

| | | | |
|---|---|---|---|
| 4,455,371 | 6/1984 | Richardson et al. | 435/28 |
| 4,655,880 | 4/1987 | Liu | 435/7.4 |

FOREIGN PATENT DOCUMENTS

| | | |
|---|---|---|
| 2806371 | 8/1979 | Germany. |
| 63-074500 | 1/1988 | Japan. |

OTHER PUBLICATIONS

C.S. Pundir, Verma, U. (1993) "Isolation, purification, immobilization of oxalate oxidase and its clinical applications," *Hindustan Antibiotics Bulletin*, vol. 35, No. 1–2, Feb., pp. 173–182.

K.V. Inamdar et al. (1989) "Determination of urinary oxalate with disposable oxalate oxidase membrane strips," *Analytical Letters*, vol. 22, No. 4, pp. 841–851. Month not available.

G.P. Kasidas, Rose, G.A. (1985) "Continuous–flow assay for urinary oxalate using immobilised oxalate oxidase," *Annals of Clinical Biochemistry*, vol. 22, No. 4, Jul., pp. 412–419.

V. Ph. Kotsira, Clonis, Y.D. (1997) "Oxalate oxidase from Barley Roots: purification to homogeneity and study of some molecular, catalytic, and binding properties," *Archives of Biochemistry and Biophysics*, vol. 340, No. 2, Apr., pp. 239–249.

R. Bais et al. (1980) "Oxalate determination by immobilized oxalate oxidase in a continuous flow system," *Analytical Chemistry*, vol. 52, No. 3, pp. 508–511. Month not available.

N. Potezny et al. (1983) "Urinary oxalate determination by use of immobilized oxalate oxidase in a continuous–flow system," *Clinical Chemistry*, vol. 29, No. 1, pp. 16–20. Month not available.

Costello et al. (1976) "An enzymic method for the spectrophotometric determination of oxalic acid" *J. Lab. Clin. Med.* 87(5):903–908. Month not available.

Chiriboga, J. (1966) "Purification and Properties of Oxalic Acid Oxidase" *Arch. Biochem. Biophys.* 116:516–523. Month not available.

(List continued on next page.)

*Primary Examiner*—Louise N. Leary
*Attorney, Agent, or Firm*—Saliwanchik, Lloyd & Saliwanchik

[57] ABSTRACT

The subject invention pertains to a novel assay device for detecting oxalate in a sample. The assay device comprises enzyme and dye compositions immobilized on a solid carrier matrix. The subject invention can also be used to measure the concentration of oxalate in a sample. The subject invention further pertains to a novel oxalate oxidase composition and methods of preparing the subject enzyme composition. The oxalate oxidase composition can be used in the assay device of the subject invention.

13 Claims, 1 Drawing Sheet

OTHER PUBLICATIONS

Laker, M.F., A.F. Hofmann, B.J.D. Meeuse (1980) "Spectrophotometric Determination of Urinary Oxalate with Oxalate Oxidase Prepared from Moss" Clin. Chem. 26(7):827–830. Month not available.

Santamaria, J.R., R. Coll, E. Fuentespina (1993) "Comparative Study of Two Commerial Enzymatic Kits for Determining Oxalate Concentrations in Urine" Clin. Biochem. 26:93–96. Month not available.

Smith, Lynwood H. (1991) "Diet and Hyperoxaluria in the Syndrome of Idiopathic Calcium Oxalate Urolithiasis" Am. J. of Kidney Diseases XVII(4):370–375. Month not available.

Sugiura, M., H. Yamamura, K. Hirano, M. Sasaki, M. Morikawa, M. Tsuboi (1979) "Purification and Properties of Oxalate Oxidase from Barley Seedlings" Chem. Pharm. Bull. 27(9):2003–2007. Month not available.

Thun, M.J., S. Schober (1991) "Urolithiasis in Tennessee: An Occupational Window Into a Regional Problem" American Journal of Public Health 81(5):587–591. Month not available.

Yriberri, J. and S. Posen (1980) "A Semi–Automatic Enzymic Method for Estimating Urinary Oxalate" Clin. Chem. 26(27):881–884. Month not available.

1

MATERIALS AND METHODS FOR DETECTING OXALATE

This invention was made with government support under grant number 5PO1DK20586 awarded by the National Institute of Health. The government has certain rights in this invention.

BACKGROUND OF THE INVENTION

Urinary oxalate concentration is an important risk factor in patients that are predisposed to kidney stone formation (nephrolithiasis). Oxalate concentration is also used for diagnosis of urolithiasis and primary hyperoxaluria (Thun et al., 1991). The normal range of oxalate excretion in urine is about 0.5 to 1.5 mM/dl (Smith, 1991). Most current methods of measuring urinary oxalate levels rely on expensive and time-consuming techniques that involve solvent extraction, spectrophotometric determinations or high performance chromatography and, therefore, are of little practical value in a clinical setting.

U.S. Pat. No. 4,455,371 (Richardson and Obzansky) describes an oxalate oxidase composition that is used in a method to assay for oxalate. Oxalate oxidase oxidizes oxalate molecules to carbon dioxide and hydrogen peroxide. An assay for oxalate using oxalate decarboxylase to convert oxalate to carbon dioxide and formate has also been described (Costello et al., 1976; Yriberri et al., 1980; Santamaria et al., 1993). Methods for detecting either the carbon dioxide, hydrogen peroxide or formate produced from the enzymatic reaction are then employed to indirectly detect the presence of the oxalate. For example, formate dehydrogenase can be used to reduce NAD to NADH in the presence of formate. The NADH produced can be detected spectrophotometrically. However, these assays for oxalate are time-consuming and require the use of complicated equipment.

The isolation and purification of oxalate oxidase compositions from moss, barley and beet stems has been described in the art (Chiriboga, J. 1966; U.S. Pat. No. 4,455,371). The methods described require extensive purification procedures and result in relatively low enzyme yield and specific activity. In addition, these oxalate oxidase compositions can be susceptible to temperature variations and are unstable when stored for extended periods. These enzyme preparations may also require the addition of exogenous co-factors to catalyze the enzymatic reaction. Oxalate oxidase compositions are also available from commercial sources (Sigma Chemical Co., St. Louis, Mo.) but suffer from similar problems.

"Dip and read" or "Dipstick" assays are currently used to measure urinary glucose levels (e.g., "TES-TAPE," Eli Lilly), determine microalbuminuria, determine urine specific gravity, detect bacteria or viruses, determine cholinesterase activity in human plasma, and the like. Urinary glucose dipsticks are categorized as enzymatic test strips, in which the substrate (e.g., glucose) is oxidized by an enzyme to yield a detectable signal. Based on the signal detected on the dipstick, which is usually manifested as a color or shade of color, the concentration of an analyte in a sample can be readily determined.

Dipstick-based assays can provide an inexpensive and rapid method for detecting or measuring the amount of a specific analyte in a sample. Moreover, the simplicity and ease of use of dipstick-based assays makes them suitable for patient self-screening or monitoring on a routine basis. Thus, dipstick-type assays have an important clinical utility.

Published Japanese patent application No. 63074500 discloses a dipstick assay that utilizes oxalate oxidase for detecting oxalate in a sample. However, this assay lacks sensitivity for oxalate concentrations below about 2 mg/dl and the oxalate oxidase enzyme used with the device may suffer from instability or degradation during its shelf life or as a result of environmental factors. In addition, the other enzyme compositions taught in the art suffer similar shortcomings and, therefore, are also unsuitable for use with a dipstick-based assay for detecting oxalate.

Accordingly, there remains a need in the art for a sensitive, rapid and stable assay system to detect oxalate in a sample, the requirements of which are met by the present invention. A dipstick assay of the present invention for determining urinary oxalate levels, comprising an enzyme and dye-based assay system, is inexpensive to make and administer, would not require laboratory equipment or experience, and could be performed in significantly less time than current techniques.

SUMMARY OF THE INVENTION

The subject invention concerns a novel assay device and methods for detecting oxalate in a sample. The assay device comprises enzyme and dye compositions immobilized on a carrier matrix. The assay device of the invention is contacted with a sample to be analyzed and a detectable color reaction develops on the carrier matrix if oxalate is present in the sample. The concentration of oxalate in a sample can be determined by comparing the color or color intensity that is observed on the carrier matrix with a color chart that was precalibrated using different concentrations of oxalate. The assay device of the subject invention can be used to detect oxalate in a variety of samples, including urine, blood, plasma, bile, saliva and other biological fluids. Accordingly, it is an object of the present invention to provide a sensitive, rapid, and stable assay for the detection and measurement of oxalate in a sample.

The subject invention further concerns a novel oxalate oxidase enzyme composition and methods for producing the oxalate oxidase composition. The oxalate oxidase produced according to the subject invention provides an enzyme having greater specific activity and yield. The enzyme of the present invention is isolated using fewer purification steps than other oxalate oxidase compositions described in the art. Moreover, the oxalate oxidase composition of the present invention is advantageously more stable and does not require the addition of exogenous co-factors for enzymatic activity unlike other oxalate oxidase preparations. The oxalate oxidase produced and isolated according to the subject invention can be utilized with the assay device and method of the present invention to detect and measure the concentration of oxalate in a sample.

DETAILED DESCRIPTION OF THE INVENTION

Figure 1:
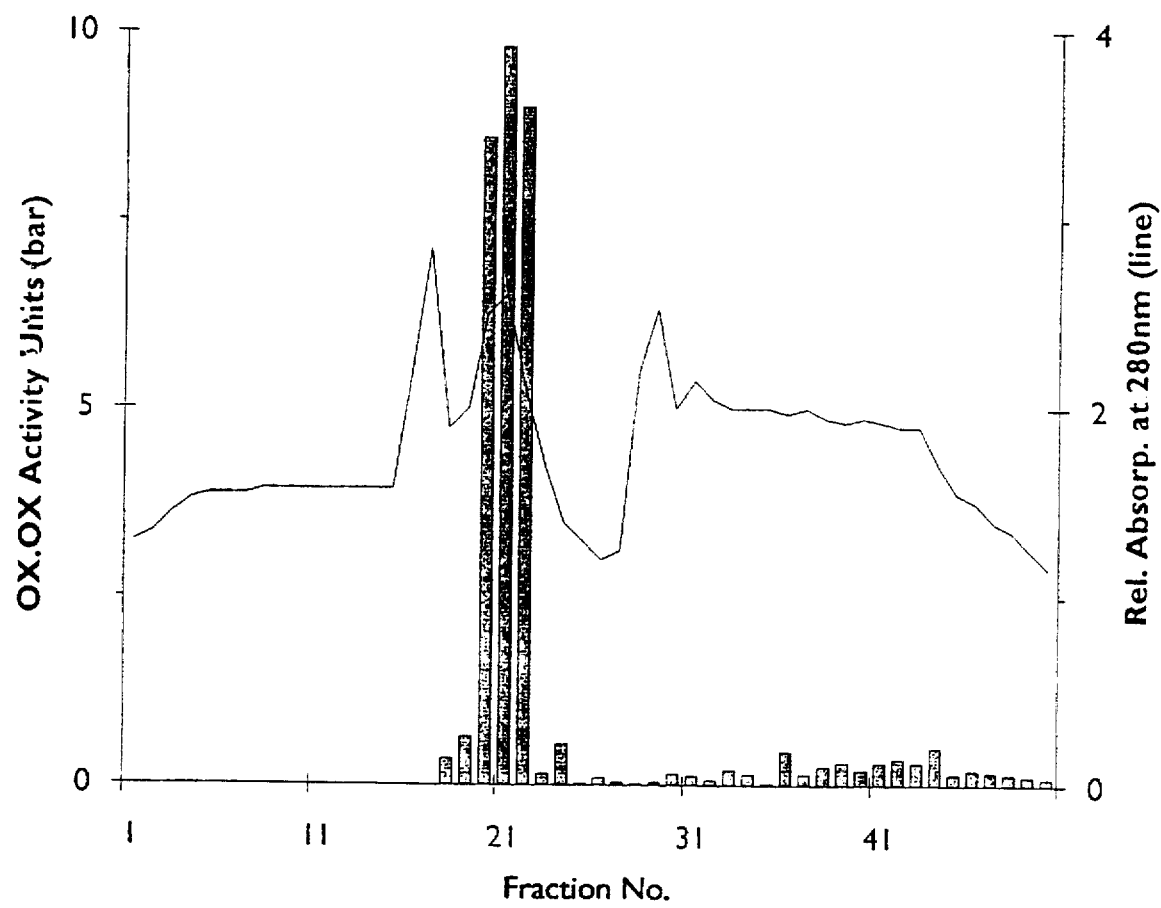
FIG. 1 shows the isoelectric focusing profile of oxalate oxidase from barley. Proteins purified by ammonium sulfate precipitation (30/60 ASP), resuspended and dialyzed against 1% glycine, were introduced into a preparative isoelectric focusing column with carrier ampholines (pH 2.5 to 5.0) in a sucrose gradient. After electrophoresis at 1500 v for 22 hours at 5° C., fractions (1 ml) were removed and continuously scanned at 280 nm (line graph), then individually dialyzed, and assayed for oxalate oxidase activity (bar graph) as described in the Materials and Methods section. Only the earlier eluted fractions of the gradient profile are shown.

The subject invention concerns a novel assay device for detecting oxalate in a test sample. The assay device of the subject invention comprises enzymes and dye components immobilized on a carrier matrix. The enzyme components used with the subject device are capable of reacting with oxalate as a substrate to produce a first reaction product. The first reaction product can react with the dye components on the carrier matrix to produce a detectable second reaction product or response that is correlated to the amount of oxalate in the sample being tested.

In a preferred embodiment, the enzyme components of the assay device comprise oxalate oxidase and a peroxidase. The oxalate oxidase can be prepared from plant tissues. The oxalate oxidase impregnated or immobilized on the carrier matrix is contacted with a sample to be tested and reacts with oxalate in the test sample and oxygen to produce hydrogen peroxide and carbon dioxide. The hydrogen peroxide produced further reacts with a peroxidase of the assay system to produce nascent oxygen, the first reaction product. The nascent oxygen thereby produced then reacts with a dye component on the carrier matrix to produce a second reaction product or response that can be detected on the matrix. Preferably, the detectable reaction product is a particular color or shade of color that is formed on the carrier matrix.

The dye composition of the assay device is a dye that can be oxidized by the first reaction product to a detectable oxidized form. Preferably, the dye is ortho-tolidine. In another embodiment of the present invention, the dye composition comprises dimethylaminobenzoic acid (DMAB) and 3-methyl-2-benzothiazolinone (MBTH). In an alternate embodiment, N,N-dimethylaniline (DMA) can be substituted for DMAB. These dye components can react with nascent oxygen, which is produced upon the reaction of the enzyme components with oxalate, to form an indamine dye which is blue in color. Other dye compositions are known in the art and are contemplated for use in the subject invention.

The carrier matrix of the assay device can be composed of any substance capable of being impregnated with the enzyme and dye components of the subject invention, as long as the matrix is substantially inert with respect to the analyte being assayed for. Preferably, the carrier matrix is porous and/or absorbent relative to the sample to be tested. The expression "carrier matrix" refers to either bibulous or nonbibulous matrices which are insoluble in water, and maintain their structural integrity when exposed to water or to other physiological fluids. Suitable bibulous matrices which can be used include paper, cellulose, wood, synthetic resin fleeces, woven and nonwoven fabrics and the like. Paper is a preferred carrier matrix. Nonbibulous matrices includes glass fiber, polymer films, preformed or microporous membranes and plastic materials, such as polypropylene and the like.

In one embodiment of the assay device, purified chromatography paper can be impregnated with the enzyme and dye components of the present invention. A strip of paper, plastic, or wood with a piece of absorbent material (e.g. cotton, synthetic fibers, or slab of polymer) attached at the tip can be employed in a similar manner. A piece of cloth can be impregnated with a polymer (e.g., the polymers used to immobilize the dye system) containing the enzyme and dye components. The polymer acts as a laminate adding rigidity to the material. The cloth may be woven of natural fibers (e.g., cotton) or synthetic fibers (e.g., polyethyleneteraphthalate). A polymer matrix, such as porous polyurethane or spunbond polyolefin, which has been impregnated with the enzyme and dye compositions of the present invention can also be employed. Any improvements in conventional solid support materials used with the carrier matrix are also encompassed within the scope of the invention.

Incorporation of the enzyme, dye and other reagent components on the carrier matrix can be accomplished by any method such as dipping, spreading or spraying. A preferred method is impregnation of the carrier matrix material by dipping in a reagent solution and drying to remove solvent. Drying can be accomplished by any means which will not deleteriously affect the reagents incorporated, and typically is by means of an air drying oven.

Wetting agents (e.g., a dilute surfactant) can be employed to increase the efficiency of the carrier matrix. Reagent alcohol can also be added to the dye system solution to accelerate the drying process once the carrier matrix is coated with the enzyme and dye components.

Reagents and solutions known in the art can be employed to stabilize and immobilize the enzyme and dye components of the subject invention to a carrier matrix. For example, salts and buffers may be used to preserve the activity of the enzyme and dye components. Ammonium sulfate, phosphate buffer, buffered salines, citrate, and succinic acid, among others, can be used to maintain pH at an optimum level (e.g., pH 3.5 for oxalate oxidase). Sugar solutions can also be used to maintain the activity of the enzyme and dye components over time. A trehalose solution can also be used to enhance the stability of oxalate oxidase immobilized on a carrier matrix and stored at room temperature. For example, a solution of about 15% trehalose can be used to stabilize the activity of oxalate oxidase in the present assay device. Polymer solutions, such as alginate, chitosan, acrylic acid, and carboxymethylecellulose, can also be used to maintain the activity of dye components over time. Other components such as thickeners, color stabilizers, surfactants or the like can also be added. The addition of a polymer such as polyvinylpyrrolidone can be used to increase stability and the uniformity of color formation on the test device.

The addition of certain minerals can increase the activity (rate at which an enzyme catalyzes a reaction) of specific enzymes. For example, copper ions enhance the activity of oxalate oxidase isolated from leaves of grain sorghum. One can also add one or more natural products to the assay device to increase the activity of specific enzymes (e.g., riboflavin enhances the activity of oxalate oxidase isolated from barley seedlings). Chelating agents, such as EDTA, can also be incorporated in the assay device to remove certain minerals which can decrease the activity of specific enzymes (e.g., iron ions inhibit the activity of oxalate oxidase isolated from barley seedlings). The chelation of calcium helps prevent the precipitation of calcium oxalate salts. The use of other agents to enhance enzymatic activity is known in the art.

The amount of oxalate present in a test sample can be semi-quantitatively determined by visually comparing the degree of the color development on the matrix with a standardized color chart that has been correlated to known concentrations of oxalate. Accordingly, it is preferable that the dipstick be uniformly wetted with the test sample so that a density of the color can be judged over a wide range of concentrations and to provide for stable color tone after the color development. In this respect, the assay device of the present invention provides for excellent sensitivity, color stability and a wide color density range. In addition to visual comparison, various instrumental methods can also be employed to detect the intensity or amount of the reaction product present on the carrier matrix.

The color range of the present assay device when oxalate oxidase is employed as an enzyme component can be expanded by adding certain dyes to the carrier matrix. For example, the incorporation of FDC Yellow No. 5 dye coloring to the carrier matrix along with a dye component such as ortho-tolidine of the present assay device provides for a detectable color that changes from yellow to green to blue to purple in proportion to the concentration of oxalic acid in a sample. The different colors or shades thereof make it easier to distinguish between various concentrations of oxalate, particularly at lower concentrations of oxalate in a test sample. The yellow dye does not interfere with the color development of the assay device. Other dyes known in the art can be used with the present invention.

In one embodiment, the assay device of the present invention can detect oxalate in a sample at concentrations as low as about 1.0 to about 0.5 milligrams (mg) per deciliter (dl).

Other enzyme compositions which react with oxalate are contemplated for use with the subject invention. In addition, any enzyme with peroxidase activity can be used in conjunction with the oxalate oxidase and assay device of the subject invention. For example, soy bean peroxidase (Enzymol International, Inc.) may be used in lieu of horse radish peroxidase in conjunction with oxalate oxidase in the assay device. By modifying the assay methods of the subject invention (i.e., the components of the assay device which react with the substrate), other factors related to oxalate levels can also be measured.

The subject invention also concerns a method for detecting or measuring the amount of oxalate in a sample. In a preferred embodiment, a dipstick assay device of the present invention is contacted with a sample for an effective period of time. Typically, the device is contacted with the sample for between about 1 to about 5 minutes. Any oxalate that may be present in the sample can react with the enzyme and dye components to produce a detectable reaction product. Preferably, the detectable reaction product is a visible color or shade of color deposited on the carrier matrix of the assay device. The amount of oxalate present in the sample can be determined by comparing the intensity or shade of color deposited on the assay device to a precalibrated oxalate concentration color chart.

In a preferred embodiment, the test sample to be assayed with the device is a biological sample or specimen. More preferably, the biological sample comprises urine, blood, plasma, bile, saliva or other biological components from an individual or subject animal.

The subject invention further concerns a novel oxalate oxidase composition and methods for producing it. Advantageously, oxalate oxidase prepared according to the present invention has greater specific activity and enzyme yield from fewer purification steps than other methods of obtaining oxalate oxidase compositions. In addition, the oxalate oxidase of the subject invention is more stable and does not require the addition of exogenous co-factors for activity. The stability of the oxalate oxidase composition to temperature, low pH, ethyl and isopropyl alcohols, acetone, lyophilization, anionic detergents, and microencapsulation makes this preparation highly desirable for numerous medical and industrial uses in both the soluble and immobilized state.

A further aspect of the present invention concerns methods for preparing oxalate oxidase compositions useful in the present assay device. The oxalate oxidase can be isolated from plant tissue. In a preferred embodiment, oxalate oxidase is prepared from germinated seeds that are frozen and then thawed during the extraction of the enzyme from the plant tissue. More preferably, the seeds are quick frozen by immersion in liquid nitrogen and then thawed during homogenization of the tissue in the initial stage of purification. Typically, the seeds used are barley seeds (*Hordeum vulgare*). Preferably, the seeds are germinated by immersion in water and under conditions which exclude light during germination (etiolated). The ability to freeze the germinated seedlings without significant loss of enzyme activity allows large quantities of source material to be accumulated and stored until it is ready to be used.

In a preferred embodiment, oxalate oxidase of the present invention is isolated by homogenizing frozen plant tissue and filtering the liquid extract obtained after homogenization to remove particulate matter. Optionally, PMSF and/or EDTA can be included during the purification of the enzyme. The liquid extract is then centrifuged and the supernatant removed from the pelleted material. The supernatant is then heat-treated. Preferably, the supernatant is heated to between about 70° and 80° C. for between about 5 to 12 minutes. More preferably, the supernatant is heated to about 75° for about 10 minutes. After heat-treatment, the supernatant is chilled close to freezing. Preferably, the supernatant is chilled to between about 3° to 4° C. After chilling, the supernatant is centrifuged again to pellet precipitated material. The heat-treated supernatant is separated from the pelleted material and brought to about 30% ammonium sulfate saturation. The precipitate in the 30% saturated solution is removed, preferably by centrifugation to pellet the precipitate. The supernatant is then subsequently brought to about 60% ammonium sulfate saturation. The precipitate in the 60% saturated solution is obtained, again preferably by centrifugation. The supernatant is discarded and the precipitated material, which contains the oxalate oxidase, is resuspended in solution.

The method of the subject invention provides an enzyme yield of at least about 0.5 enzyme units per gram of starting plant tissue. Preferably, the enzyme yield is in the range of about 0.5 to 0.9, or greater, enzyme units per gram of plant tissue.

In a preferred embodiment, the oxalate oxidase prepared by the method of the present invention has a specific activity of at least about 8.5 enzyme units per milligram of protein. Preferably, the oxalate oxidase has a specific activity of at least about 10 enzyme units per milligram of protein. More preferably, the oxalate oxidase composition of the subject invention has a specific activity of at least about 20 enzyme units per milligram of protein. Most preferably, the oxalate oxidase composition of the subject invention has a specific activity of between about 30 to 60 enzyme units per milligram of protein.

Optionally, the oxalate oxidase can be further purified by isoelectric focusing and collecting the fractions between about pH 2.5 and 3.0.

MATERIALS AND METHODS

Materials. Wysor barley, lot #6321-38B, from Wetsel Seed Co., treated with VITAVAX 200 (fungicide) and RELDAN (insecticide) and Venus barley, lot #BSCNC87-197 from Food Science and Human Nutrition, University of Florida, were used in the production of oxalate oxidase. Seed was distributed in 1 kg lots in sealed plastic bags and stored at 4°–6° C. Biogel wrap was from BioDesign of New York. Oxalate oxidase, horse radish peroxidase (Type VI) electrophoresis standard proteins, bovine serum albumin, enzyme grade ammonium sulfate, phenylmethylsulfonylfluoride (PMSF), and Coomassie blue R were obtained from Sigma Biochemicals (St. Louis, Mo.). PHARMA-LYTE carrier ampholines were from Pharmacia LKB Biotechnology (Uppsala, Sweden). MIRACLOTH (glass paper) was from Cal Biochem Inc.

Seedling germination, harvesting, and storage. Seeds were germinated in 1 kg batches in a perforated, plastic pipet basket by immersion in tap water for 24 hours at 23° to 26° C., followed by incubation beneath a shower of tap water, with shaking twice a day, for seven to nine days. Spreading imbibed seed over a cheesecloth-lined plastic rack beneath the shower and enclosing the system in a black plastic polyethylene curtain to exclude light enhanced the germination rate, favored root growth, and facilitated harvesting the appropriate tissue. After incubation, whole seedlings were blotted to remove excess water and harvested directly into liquid nitrogen. The frozen tissue was stored in covered plastic specimen cups (120 to 130 g) at −70° C.

Oxalate oxidase activity assays. Oxalate oxidase activity was determined using a modification of the spectrophotometric assay method of Laker et al. (1980) for urinary oxalate. Fresh dye reagent containing 250 µl oxalic acid (200 mM), 2.5 ml sodium succinate, pH 4.0 (0.25M), 250 µl 3-methyl-2-benzothiazolinone hydrazone (2.5 g/l in 0.1M HCl), 1.25 ml N,N-dimethylaniline (2.5 g/l in 0.1M HCl), and 350 units horse radish peroxidase was brought to 25 ml with glass distilled water in an amber bottle. A sample aliquot (10 to 200 µl) in a plastic microcuvette (1 cm light path) was diluted to 200 µl with 25 mM sodium succinate buffer. At zero time, 2.0 ml of the dye reagent was added to the cuvette with mixing, incubated at 23° C. in the dark, and then read at 595 nm at 2 or 5 minute intervals for 8 or 20 minutes. Samples were read against a buffer blank, i.e., a microcuvette containing the same dye reagent but without the oxidase sample added in. One Enzyme Unit of activity is defined as an increase in absorbance at 595 nm of one per minute at 23° C.

Alternatively, a semi-quantitative assay was utilized for the presumptive detection of oxidase activity. 100 µl of the above dye reagent was placed in one well of a plastic microtitre plate. 10 µl of sample was added with mixing and incubated at room temperature for 5 to 60 minutes. Development of a purple color was observed visually and the relative intensity scored (0 to 4) against that of a well containing dye reagent devoid of sample.

Protein assay. The concentration of trichloroacetic acid-insoluble protein was estimated spectrophotometrically by the bicinchoninic acid method (BCA) of Smith et al. (1985) using bovine serum albumin (BSA) as a standard. Color was developed by incubation at 60° C. for 30 minutes, followed by cooling in ice water prior to reading.

Enzyme preparation. 275 g of frozen barley tissue from etiolated seedlings and 3 ml of phenylmethylsulfonyl fluoride (PMSF) (10 mg/ml in isopropanol) were added to 600 ml of 0.1 mM ethylenediaminetetraacetic acid (EDTA) in a teflon-lined, commercial blender. The mixture was ground at high speed for 15 seconds, twice, to a consistency approximating oatmeal, and immediately filtered through 4 layers of cheesecloth into a cold cylinder. The remaining liquid was expressed from the tissue by manually squeezing the bolus in the cheesecloth. This yielded about 800 ml of extract at pH 5. The extract was immediately centrifuged at 20,000×g for 20 minutes at 0° C. and the clear, amber low speed supernatant (LSS) decanted into a two liter round-bottom flask. The flask was mounted on a rotating evaporator (no vacuum) with the flask immersed in a water bath at 84° C. The temperature of the LSS was raised to about 75° C. in 10 minutes, then immediately chilled in an ice bath, centrifuged as described above, and the heat treated supernatant (HTS) retained. The HTS, at pH 5, was brought to 30% saturation by adding freshly powdered ammonium sulfate ($(NH_4)_2SO_4$, 175.7 g/l) with constant stirring. Stirring was continued for 30 minutes at 0° C. and the mixture was then centrifuged as above for 10 minutes. The clear, amber supernatant fraction was decanted into a cold beaker and brought to 60% saturation by the addition of more ammonium sulfate (195 g/l) as described above. The white material that collected at the solution surface was removed, and the mixture again centrifuged as described above. The supernatant fraction was discarded, the pellets drained, and the bottle walls opposite the pellets wiped free of debris. The pellets were suspended in 70 ml of 0.1 mM EDTA, 100 µg/ml PMSF and dialyzed against four liters of distilled water for 36 to 48 hours at 4° C., unless noted otherwise. This preparation is referred to herein as the 30/60 ASP preparation. The dialyzed 30/60 ASP preparations were centrifuged at 10,000×g for 10 minutes to clarify, if necessary, and lyophilized at −60° C.

Isoelectric focusing. Samples were introduced into a 110 ml LKB preparative column with a 1% PHARMALYTE pH 2.5-5 carrier ampholine gradient in 5 to 60% sucrose (Sugiura et al., 1979). Proteins were focused for 22 hours at 5° C. with a initial current of 7 mA at a constant potential of 1500 v (anode at the bottom) according to the method of Vesterberg and Svensson (1966). After stabilization of the current at 3.1 mA (22 hours), the resolved components were collected by hydrostatic displacement from the bottom of the column in 1 ml fractions at 1 ml/min and continuously scanned at 280 nm. Each fraction was dialyzed at 5° C. against 0.1M NaCl, 5 mM sodium succinate, pH 4.1, 50 µg/ml PMSF for 20 hours to remove the ampholines and against 5 mM sodium succinate, pH 4.1, 50 µg/ml PMSF for 24 hours, successively, to remove the salt prior to assay.

Lyophilization. Dialyzed preparations (centrifuged at 10,000×g for 10 minutes at 0° C. to clarify, if necessary), were decanted into a 600 ml Virtis flask, frozen as a shell on the flask wall by immersion in a dry ice/acetone bath, and lyophilized overnight at −60° C. Dry samples were transferred to screw cap bottles, tightly capped and stored at −20° C.

Following are examples which illustrate materials, methods and procedures, including the best mode, for practicing the invention. These examples are illustrative and should not be construed as limiting.

EXAMPLE 1

Seedling Germination for Isolation of Oxalate Oxidase

Trials with 200 seeds each (Wysor barley) were undertaken to optimize germination conditions. After imbibition for 21 hours in tap water, seeds were spread on trays lined with three layers of Whatman #3 filter paper, wetted with tap water and incubated in constant fluorescent light or in darkness at 23° C. for seven days. Alternatively, imbibed seeds were placed in a perforated plastic basket under a shower of tap water (23° C.) for seven days. Maximum germination occurred with seed in the tray incubated in the dark. Those seeds exhibited a preponderance of root emergence. Upon prolonged germination, no more shoots emerged and no further increase in germination rate was noted on the trays. However, continued incubation of the seeds under the tap water shower increased both the number of seed germinated and the amount of tissue generated per seedling. Since the objective was to obtain large amounts of tissue, the shower mode of germination was modified to accommodate larger amounts of grain (See the Materials and Methods section). Yields typically ranged from about 1 kg to about 3.6 kg of frozen tissue (roots, grain, and shoots) per 1 kg of dry seed. A preparation from green sprouts, pruned from the seedlings and frozen separately yielded no activity; thus, efforts were made to exclude light during germination.

EXAMPLE 2

Preparation of Barley Oxalate Oxidase Compositions

Oxalate oxidase was purified as described in the Materials and Methods section. Particulate material in the initial tissue homogenate precluded a quantitative assay of oxalate oxidase activity. However, using the semi-quantitative microtitre plate assay it was determined that less than half of the oxalate oxidase activity detected in the homogenate was recovered in the low speed supernatant (LSS). Contamination with insoluble starch in the root-rich preparation was minimized by selectively harvesting shoot and root tissue to the exclusion of the ungerminated barley grains.

The addition of PMSF (dissolved in isopropanol) to the initial tissue homogenate dramatically altered the behavior and the appearance of the barley extract and successive fractions derived from it. The cloudy opalescence in supernatant fractions was eliminated and the pellets obtained upon centrifugation were discrete and compact. In one preparation, an eight-fold enrichment in oxalate oxidase activity with a ten-fold concentration of protein was obtained from tissue homogenates prepared in the presence of PMSF. More than 90% of the enzymatic activity detected in the low speed supernatant was recovered in the ammonium sulfate precipitated proteins (See Table 1).

TABLE 1

Enrichment of oxalate oxidase isolated from barley seedlings.

| Fraction | Vol.[1] (ml) | Total Activity (units)[2] | Specific Activity[3] (units/mg) | Yield (units/g tissue) |
|---|---|---|---|---|
| LSS (Low Speed Supernatant) | 720 | 276 | 1.08 | 1.00 |
| HT (Heat Treated) | 720 | 171 | 0.62 | 0.62 |
| HTS (Heat Treated Supernatant) | 705 | 168 | 0.68 | 0.61 |
| 30/60 ASP (Ammonium sulfate ppt. between 30 and 60% saturation) | 72 | 257 | 8.50 | 0.93 |

[1]Fraction dialyzed prior to assay.
[2]Unit of activity is the change in absorption at 595 nm per minute in the spectrophotometric assay defined in the Materials and Methods section.
[3]Protein determined with BCA as described in the Materials and Methods section.

Further purification of the 30/60 ASP oxalate oxidase preparation was achieved by preparative isoelectric focusing of this material between about pH 2.5 and 5.0. A 30/60 ASP fraction (43 ml), prepared in the presence of PMSF and dialyzed against four liters of 1% glycine for 45 hours was immediately loaded with a sucrose/PHARMALYTE gradient into a cooled focusing apparatus. The sample was focused for 22 hours and 1 ml fractions collected and prepared for assay as described in the Material and Methods section. As seen in FIG. 1, essentially all of the recovered activity (55% of that applied) was focused as a single peak. A band of tan precipitate was visible in the lower portion of the column. The oxalate oxidase obtained after isoelectric focusing was concentrated 14-fold over the starting material, but exhibited only a slight increase in specific activity (12 units/mg). The pH of the active fractions was estimated to lie between about pH 2.75 and 2.9, assuming that the pH gradient was linear from pH 2.5 to 5.0 in 110 ml. The low levels of activity detected in the more alkaline fractions of the upper portion of the gradient corresponded to cross contamination with residual precipitated material observed as the fractions were collected from the column.

EXAMPLE 3

Preparation of Dipstick Device

A dipstick assay device according to the subject invention was prepared by saturating a 0.25 in. by 3 in. strip of high purity chromatography paper with a solution of the enzyme and dye components. The solution comprised 0.1 g carboxymethylcellulose, 150 units oxalate oxidase (the dialyzed 30/60 ASP fraction prepared as described in the Materials and Methods section), 120 PZ units horseradish peroxidase, and 4.5 mg ortho-tolidine, in 10 mL of 0.025M sodium succinate buffer (pH 4.0). The dipsticks were contacted with the solution, thoroughly coating the entire dipstick, and removed to dry. The dipsticks can be stored in a dry and dark place, preferably below 30° C., prior to use.

A dipstick coated with the enzyme and dye components as described above was contacted with a sample to be tested for the presence of oxalate. After contact with the sample, color was allowed to develop for a certain period of time and the dipstick color was then compared to a standard color chart for estimating oxalate concentration.

A concentration calibrated color chart can be prepared by dipping individual dipsticks in solutions containing oxalic acid concentrations of 1, 2, 4, 8 and 16 mM, respectively. The colors observed on the dipsticks tested with each known oxalate solution are arranged on a chart that shows a color or color intensity for a given concentration of oxalate after a specified time of development. The concentration of oxalate in a sample can be estimated by comparing the color on the test dipstick that develops after a specific period of time to the colors shown on the standardized color chart.

A dipstick device of the present invention detected oxalate in a test sample at a concentration of about 0.9 mg/dl or about 1 µM based on visual observation of the color development and comparison to the standardized color chart.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

1. Costello et al. (1976) "An enzymatic method for the spectrophotometric determination of oxalic acid" *J. Lab. Clin. Med.* 87(5):903–908.

2. Chiriboga, J. (1966) "Purification and Properties of Oxalic Acid Oxidase" *Arch. Biochem. Biophys.* 116:516–523.

3. Davis, B. J. (1964) "Disc electrophoresis. II Method and application to human serum proteins" *N.Y. Acad. Sci.* 121:404–427.

4. Japanese patent application No. 63074500, published Apr. 4, 1988 entitled "Test Strip for Detecting Oxalate in Body Fluid."

5. Laemmli, U. K. (1970) "Cleavage of structural proteins during the assembly of the head of bacteriophage $T_4$" *Nature* 220:680–685.

6. Laker, M. F., A. F. Hofmann, B. J. D. Meeuse (1980) "Spectrophotometric determination of urinary oxalate with oxalate oxidase prepared from moss" *Clin. Chem.* 26:827–830.

7. Santamaria, J. R., R. Cold, E. Fuentespina (1993) "Comparative Study of Two Commercial Enzymatic Kits for Determining Oxalate Concentrations in Urine" *Clin. Biochem.* 26:93–96.

8. Smith, P. K., R. I. Krophn, G. T. Hermanson, A. K. Mallia, F. H. Gartner, M. D. Provenzano, E. K. Fujimoto, N. M. Goeke, B. J. Oloon, D. C. Klenk (1985) *Anal. Biochem.* 150:76–85.

9. Smith, Lynwood H. (1991) "Diet and hyperoxaluria in the syndrome of idiopathic calcium oxalate urolithiasis" *Am. J. of Kidney Diseases* XVII:370–375.

10. Sugiura, M., H. Yamamura, K. Hirano, M. Sasaki, M. Morikawa, M. Tsuboi (1979) "Purification and properties of oxalate oxidase from barley seedlings" *Chem. Pharm. Bull.* 27:2003–2007.

11. Thun, M. J., S. Schober (1991) "Urolithiasis in Tennessee: An Occupational Window into a Regional Problem" *American Journal of Public Health* 81(5):587–591.

12. Vesterberg, O., H. Svensson (1966) "Isoelectric fractionation, analysis, and characterization of ampholytes in natural pH gradients. VI Further studies of the resolving power in connection with the separation of myoglobins" *Acta. Chem. Scand.* 20:820–834.

13. Yriberri, J. and Posens, S. (1980) "A Semi-Automatic Enzymatic Method for Estimating Urinary Oxalate." *Clin. Chem.* 26:881–884.

14. U.S. Pat. No. 4,455,371 issued to Richardson, K. E. and Obzansky, D. M. on Jun. 19, 1984.

We claim:

1. A process for preparing an oxalate oxidase composition comprising the steps of preparing an extract from plant tissue, wherein phenylmethylsulfonyl flouride is included during preparation of said extract, precipitating proteins in said extract by bringing said extract to at least about 30% saturation with ammonium sulfate, removing said precipitated proteins and bringing said extract to at least about 60% saturation with ammonium sulfate to precipitate said oxalate oxidase present in said extract, and recovering said oxalate oxidase.

2. The process, according to claim 1, wherein said plant tissue comprises germinated seedlings.

3. The process according to claim 2, wherein said germinated seedlings are germinated under conditions which exclude light.

4. The process according to claim 2, wherein said germinated seedlings are frozen and then thawed during the preparation of said extract from said plant tissue.

5. The process according to claim 1, wherein said plant tissue comprises barley plant tissue.

6. The process according to claim 1, wherein prior to precipitating said proteins with ammonium sulfate, said extract is heated and then subsequently chilled to between about 3° to 4° C.

7. The process, according to claim 6, wherein the step of heating said extract is at a temperature of between about 70° to 80° C. for between about 5 to 12 minutes.

8. An oxalate oxidase composition having a specific activity of at least about 10 enzyme units per milligram of protein after ammonium sulfate (($NH_4)_2SO_4$) precipitation.

9. An oxalate oxidase having a specific activity of at least about 20 enzyme units per milligram of protein after ammonium sulfate (($NH_4)_2SO_4$).

10. The oxalate oxidase according to claim 8 wherein said oxalate oxidase is produced according to a process comprising the steps of preparing an extract from plant tissue, precipitating proteins in said extract by bringing said extract to at least about 30% saturation with ammonium sulfate, removing said precipitated proteins and bringing said extract to at least about 60% saturation with ammonium sulfate to precipitate said oxalate oxidase present in said extract and recovering said oxalate oxidase.

11. A method for detecting oxalate in a test sample, comprising the steps of:

(a) contacting said test sample for an effective period of time with an assay device for detecting oxalate, wherein a detectable reaction product is produces when oxalate is present in said test sample, said assay device comprising: (i) an enzyme composition, wherein oxalate is a substrate for said enzyme composition, and wherein said enzyme composition reacts with oxalate in said sample to produce a first reaction product; (ii) a dye composition, wherein said dye composition is reactive with said first reaction product to produce a second reaction product, wherein said second reaction product can be detected; and (iii) a carrier matrix, wherein said enzyme composition and said dye composition are immobilized on said carrier matrix; and (b) detecting said oxalate by detecting the production of said reaction product.

12. The method according to claim 11, wherein said detectable reaction product comprises a visible dye on said support matrix, wherein said visible dye can be detected visually.

13. The method according to claim 11, wherein said device is contacted with said test sample for between about 1 to about 5 minutes.

* * * * *

UNITED STATES PATENT AND TRADEMARK OFFICE
CERTIFICATE OF CORRECTION

PATENT NO. : 5,776,701
DATED : July 7, 1998
INVENTOR(S) : Rusty J. Mans, Christopher D. Batich, Ian McFetridge It is certified that error appears in the above-identified patent and that said Letters Patent is hereby corrected as shown below:

Column 3, line 53-54: "(e.g. cotton, " should read --(e.g., cotton, --.

Column 12, line 13: "oxidase having" should read --oxidase composition having--.

Column 12, line 15: "(($NH_4$)$_2$$SO_4$)." should read --(($NH_4$)$_2$$SO_4$) precipitation.--.

Column 12, line 30: "is produces" should read --is produced--.

Signed and Sealed this

Second Day of March, 1999

Attest:

Q. TODD DICKINSON

*Attesting Officer*    Acting Commissioner of Patents and Trademarks